United States Patent
Chang et al.

(10) Patent No.: US 7,265,355 B2
(45) Date of Patent: Sep. 4, 2007

(54) METHOD AND SYSTEM FOR ACQUIRING FULL SPINE AND FULL LEG IMAGES USING FLAT PANEL DIGITAL RADIOGRAPHY

(75) Inventors: Yun C. Chang, Rochester, NY (US); John Yorkston, Penfield, NY (US); David H. Foos, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 165 days.

(21) Appl. No.: 10/988,101

(22) Filed: Nov. 12, 2004

(65) Prior Publication Data

US 2005/0104018 A1 May 19, 2005

Related U.S. Application Data

(63) Continuation-in-part of application No. 09/745,663, filed on Dec. 21, 2000, now abandoned.

(51) Int. Cl.
*G01T 1/24* (2006.01)

(52) U.S. Cl. .................................. 250/370.09; 378/162

(58) Field of Classification Search .............. 378/181, 378/176, 175, 164, 163, 162; 250/370.09
See application file for complete search history.

(56) References Cited

U.S. PATENT DOCUMENTS

| | | | |
|---|---|---|---|
| 3,725,703 A * | 4/1973 | Bucky | 378/174 |
| 4,162,406 A * | 7/1979 | Gieschen et al. | 378/175 |
| 4,780,897 A | 10/1988 | McDaniel et al. | |
| 4,831,260 A | 5/1989 | DiBianca | |
| 5,222,115 A * | 6/1993 | Highgenboten | 378/177 |
| 5,986,279 A | 11/1999 | Dewaele | |
| 6,052,476 A | 4/2000 | Qian et al. | |
| 6,069,362 A | 5/2000 | Giakos | |
| 6,175,609 B1 | 1/2001 | Edic et al. | |
| 6,215,848 B1 * | 4/2001 | Linders et al. | 378/98.12 |
| 6,396,903 B1 * | 5/2002 | Wenstrup | 378/164 |

* cited by examiner

*Primary Examiner*—Constantine Hannaher

(57) ABSTRACT

Apparatus for acquiring an elongated radiographic image. The apparatus includes a flat panel electronic detector of radiographic images, the detector having a known length; and a transport mechanism for mounting the detector for movement in a direction parallel to the known length so that the detector can be positioned in sequential contiguous partially-overlapping positions to acquire a radiation image greater in length than the detector length. At least one marker is disposed in a region corresponding with each partially-overlapping position of the detector.

5 Claims, 4 Drawing Sheets

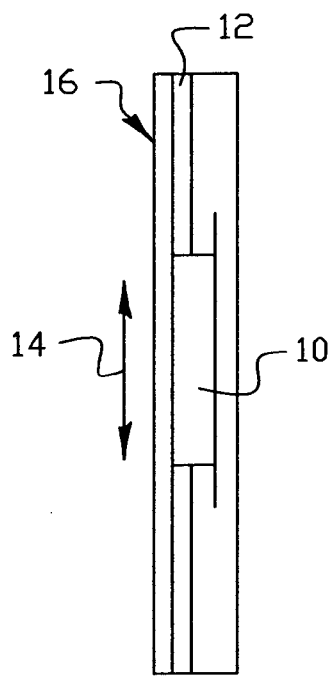
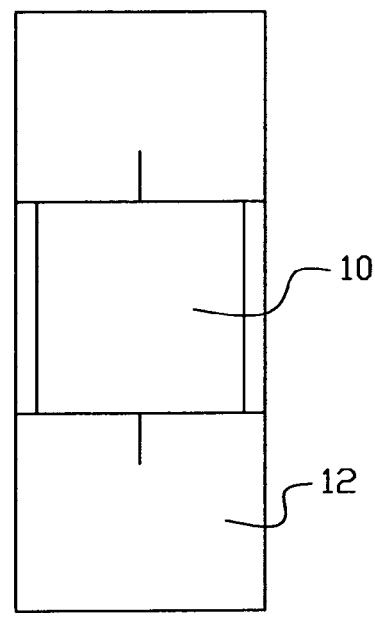
FIG. 1A                FIG. 1B
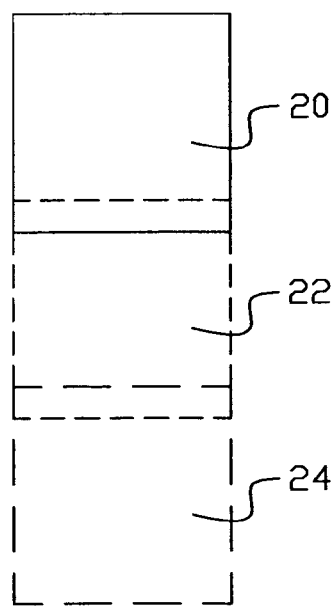
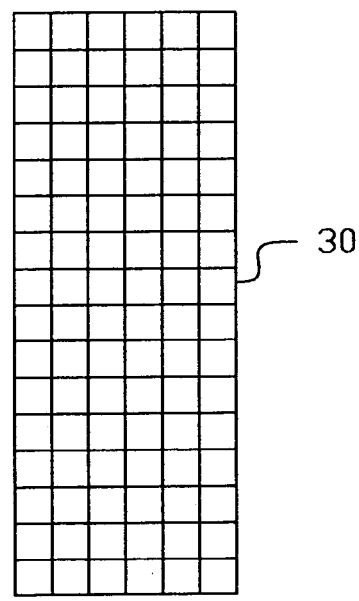
FIG. 2                 FIG. 3

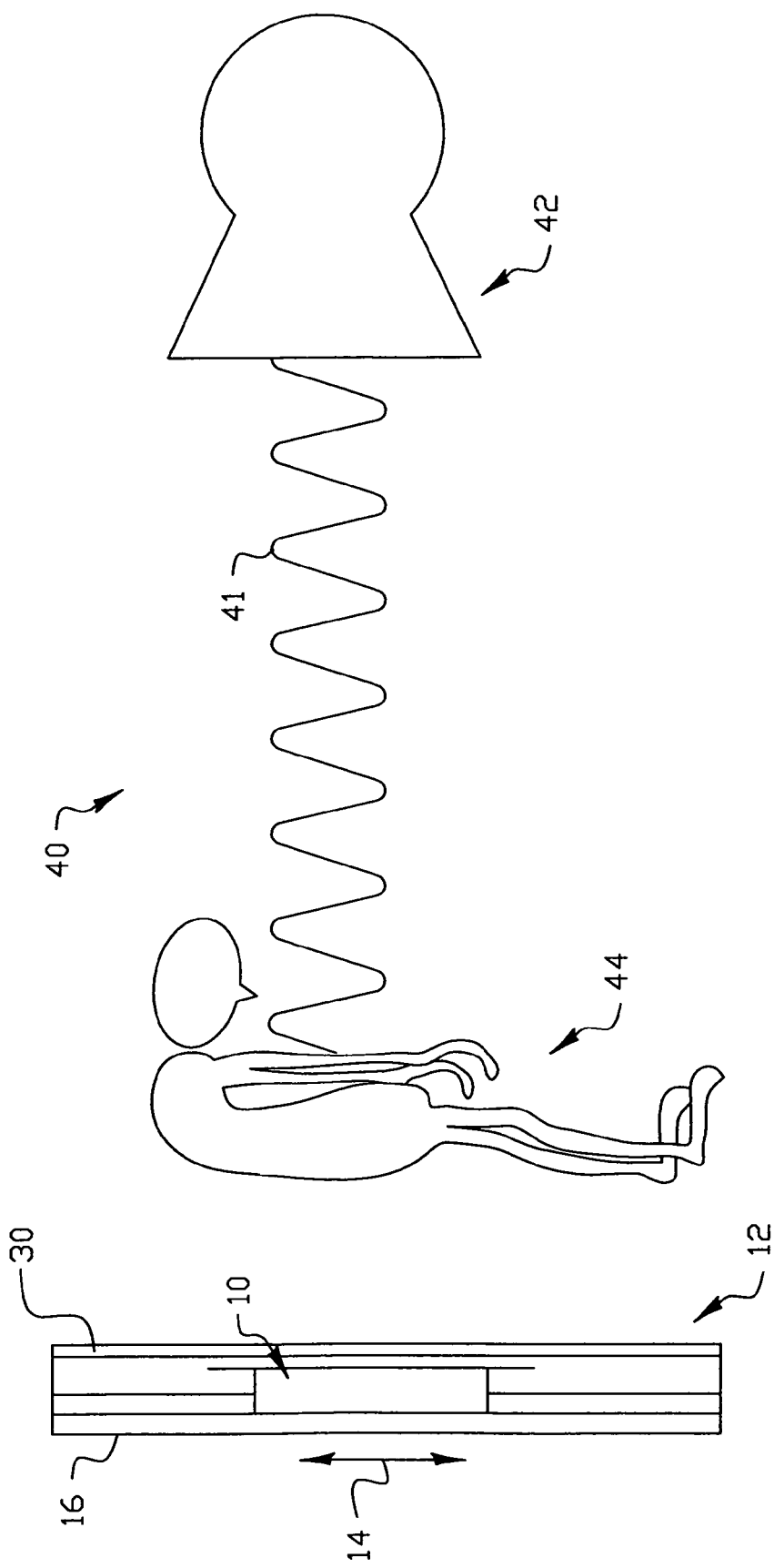

METHOD AND SYSTEM FOR ACQUIRING FULL SPINE AND FULL LEG IMAGES USING FLAT PANEL DIGITAL RADIOGRAPHY

CROSS REFERENCE TO RELATED APPLICATION

This application is a Continuation-in-Part of U.S. Ser. No. 09/745,663, filed on Dec. 21, 2000, now abandoned, commonly assigned, and incorporated herewith by reference.

FIELD OF THE INVENTION

This invention relates in general to digital radiographic imaging, and in particular to the acquisition of multiple, standard sized radiographs for purposes of constructing a larger composite radiographic image.

BACKGROUND OF THE INVENTION

Full spine and full leg radiographic examinations require images that are longer than the length of normal-sized radiographic films. The problem is circumvented by two approaches. The first approach uses an extra long, non-standard film. This approach is expensive and inconvenient. The second approach uses several normal-size films for exposure and then tape the sub-images together (see U.S. Pat. Nos. 3,725,703 and 3,774,703). Computed Radiography (CR) has the same problem. The problem is circumvented by either using an elongated CR plate (U.S. Pat. No. 5,130,542) or by using several CR plates for imaging, and then using digital image processing to stitch the sub-images together (U.S. Pat. Nos. 5,111,045, 5,986,279 and EPO 919856A1).

With the advent of flat panel digital radiography (DR), it is natural to apply the technology to full spine/leg imaging. Various patents teach the assembly of smaller sensor arrays to form a large sensor (U.S. Pat. Nos. 5,105,087, 4,467,342, and 4,755,686). However, DR sensors are expensive. Thus the DR assembly approach is economically prohibitive. One patent teaches the use of a moving sensor to detect fan beam X-ray in CT scan (U.S. Pat. No. 4,873,708). The approach takes the scanned signals and constructs a sliced image of the body. U.S. Pat. Nos. 4,613,983 and 5,123,056 disclosure systems for imaging a human subject on a table including an X-ray source, a table and an image intensifier tube. Either the table or X-ray source and table are moved to produce a series of overlapping electronic images which are combined into an elongated image for display or printing. Another patent teaches a moveable X-ray cassette holder design.

The field of DR is expanding rapidly. Physicians order full spine and full leg imaging routinely for scoliosis patients and for leg length, angulation and deformity measurements. It is therefore necessary to provide an economically feasible capability for acquiring images using flat panel digital radiography that can be used for subsequent construction of full spine and long bone images.

SUMMARY OF THE INVENTION

According to one feature of the invention, it focuses on the sequential acquisition of multiple radiographic images using a moveable DR plate for purposes of digitally constructing a composite larger spine or long bone image.

According to another feature of the present invention, a standard DR plate is mounted on a moving plate holder. Two or more radiographic images are acquired sequentially. The spatial position of each subsequent image is acquired with a small amount of overlap of the spatial position of the previous image to aid in the construction of the composite image.

Individual images are acquired in the presence of a reference grid or some other fiducial markers to aid in performing geometric corrections for distortion introduced by the image acquisition process as the DR plate is moved.

ADVANTAGEOUS EFFECT OF THE INVENTION

The invention has the following advantages.
1. Composing sub-images acquired by DR is useful for full spine and full leg radiographic examinations. This approach combines the convenience of DR with the flexibility of digital image processing.
2. Only one DR plate is used for image acquisition. The first sub-image can be processed while the second one is being taken. Both cost saving and the convenience of DR imaging can be achieved.

BRIEF DESCRIPTION OF THE DRAWINGS

FIGS. 1A and 1B are diagrammatic side and front views of a DR plate mounted on a transport mechanism that allows the plate to be repositioned for sequential image capture.

FIG. 2 is a diagrammatic view showing an example of 3 sequentially acquired DR images with a small amount of overlap between each sequential pair.

FIG. 3 is a diagrammatic view showing an example of a fiducial marker, in this example the drawing represents a fine wire grid that has precisely defined squares. The image of the patient is acquired together with the grid, or some other form of reference marker target to facilitate construction of the composite image.

FIG. 4 is a diagrammatic view of a radiographic imaging system incorporating the present invention.

DETAILED DESCRIPTION OF THE INVENTION

Figure 5:
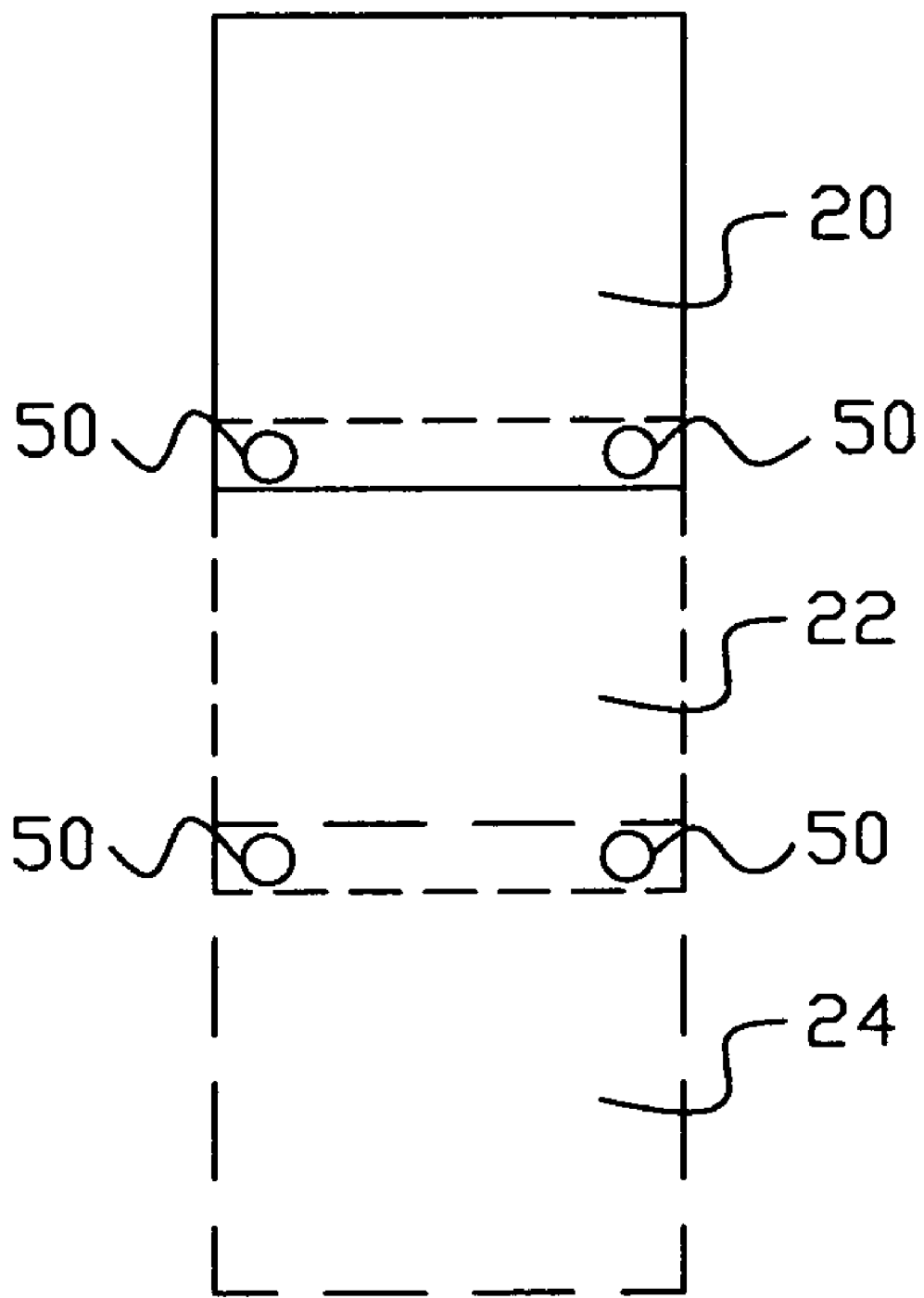
FIG. 5 is a diagrammatic view showing an example of 3 sequentially acquired DR images with a small amount of overlap between each sequential pair, illustrating fiducial markers.

The present invention enables the sequential acquisition of multiple flat panel digital radiographs using a standard sized flat panel detector in such a way as to facilitate the subsequent construction of a larger composite image. As shown in FIG. 1, the flat panel detector 10 is mounted to a transport mechanism 12 that enables the detector to be moved in the vertical (up or down) direction 14 between each image acquisition. Mechanism 12 is mounted on a frame 16. Detector 10 can be moved manually or be motor driven (not shown). The images are acquired such that there is a small amount of overlap between the previous and next acquisition. FIG. 2 shows the acquisition of 3 overlapped images 20, 22, 24. Fiducial markers are superimposed on the image of the patient so that the distortion introduced by the change in position of the detector relative to the direction of the primary radiation for sequential acquisitions can be corrected. FIG. 3 shows an elongated guide 30 of radiation opaque material, such as lead. As shown in FIG. 4, grid 30 is placed in front of DR plate 10.

Referring now to FIG. 4, there is shown a radiographic imaging system 40 incorporating the present invention. As shown, system 40 includes a source 42 of penetrating radiation, such as X-rays 41. A patient 44 is placed between source 42 and detector 10. Detector 10 is mounted for movement in the vertical direction 14 on transport assembly 12 on frame 16. Radiation attenuating grid 30 is positioned between detector 10 and patient 44.

Figure 6:
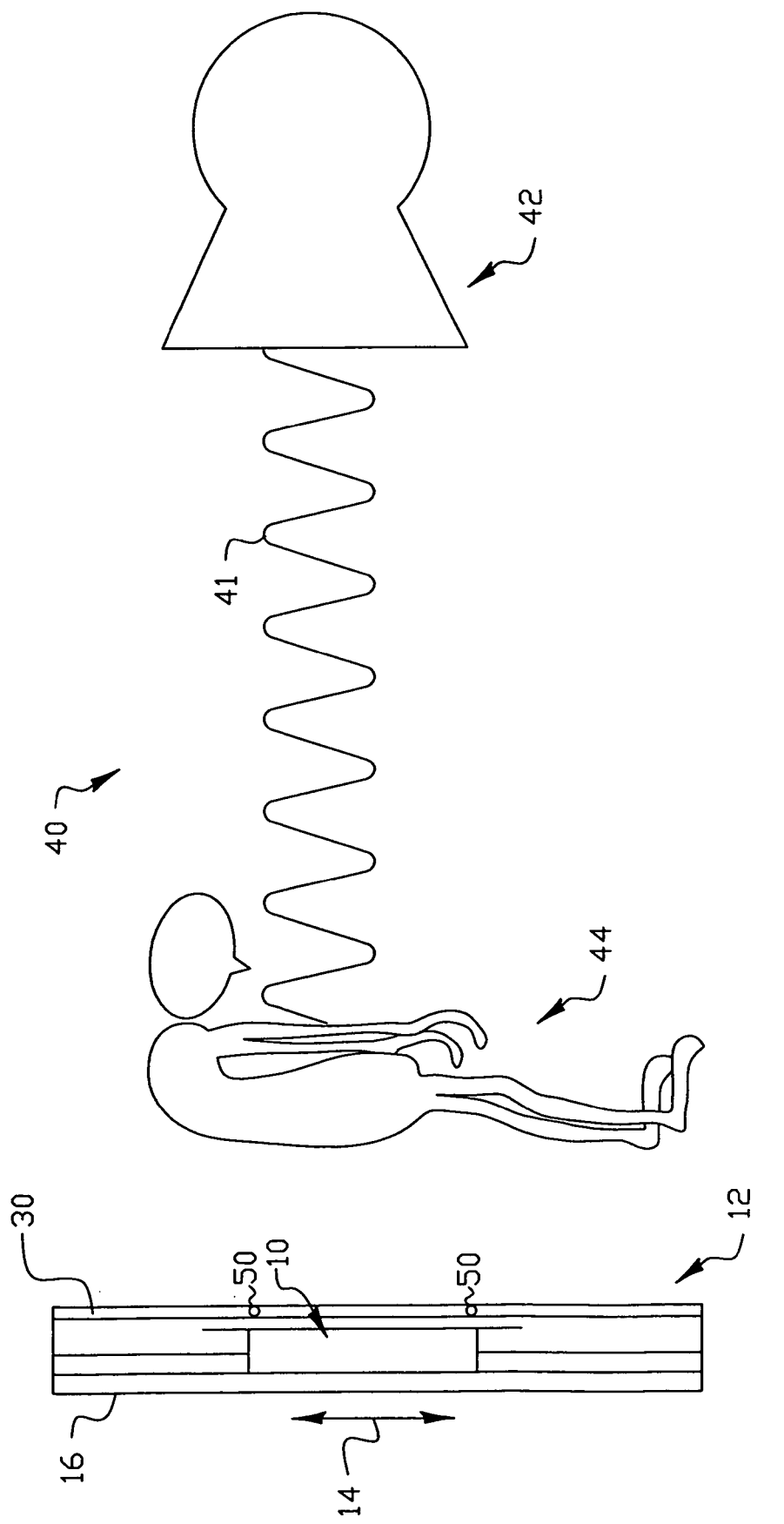
FIG. 6 is a diagrammatic view of a radiographic imaging system incorporating markers illustrated in FIG. 5.

FIGS. 5 and 6 illustrate the use of fiducial markers 50 disposed proximate an edge of frame 16. At least one fiducial marker 50 is stationarily disposed on frame 16 so as to be located in the region of the overlapping images.

Fiducial marker 50 is comprised of a radiation attenuating material or radiation opaque material, for example, lead. Fiducial marker 50 can be comprised of any shape, for example, a circle, square, triangle, and the like. Fiducial marker 50 can also be of any size, however, it should be of a size readily detectable in the acquired image, but not of a size that would interfere/obstruct/obscure the image content of the acquired image.

So as to not to interfere/obstruct/obscure the image content of the acquired image, fiducial marker 50 is disposed proximate an edge of frame 16 which is parallel to the direction of motion of transport system 12, at a location corresponding to a region of the overlapping images. (More than one marker can be disposed within the region, for example, one marker 50 along each edge of frame 16.) As such, when detector 10 is positioned and an image is acquired, at least one fiducial marker 50 will be imaged within each acquired image. The fiducial marker is superimposed on the image of the patient so that the distortion introduced by the change in position of the detector relative to the direction of the primary radiation for sequential acquisitions can be corrected.

Fiducial marker 50 provides an advantage over guide 30 in that there is no need to reconstruct the entire guide 30. Only marker 50 needs to be reconstructed.

In addition, marker 50 is simple in its shape and size. Further, marker 50 can be sufficiently large in size for detection since it is located along the edge and is not obstructing or obscuring the image content of the acquired image. Because of its size, marker 50 are not subject to tensional deformation.

The invention has been described in detail with particular reference to certain preferred embodiments thereof, but it will be understood that variations and modifications can be effected within the spirit and scope of the invention.

| PARTS LIST | |
|---|---|
| 10 | detector |
| 12 | transport mechanism |
| 14 | direction |
| 16 | frame |
| 20, 22, 24 | image |
| 30 | grid |
| 40 | imaging system |
| 42 | source |
| 44 | patient |
| 50 | fiducial marker |

What is claimed is:

1. Apparatus for acquiring an elongated radiographic image comprising:
   a flat panel digital electronic detector of radiographic images, the detector having a known length;
   a transport mechanism mounting the detector for movement in a direction parallel to the known length to position the detector in sequential contiguous partially-overlapping exposure positions to acquire corresponding individual radiation images that can be combined digitally to provide a composite image greater in length than the detector;
   a frame supporting the transport mechanism, the frame having an edge substantially parallel to the direction of movement of the detector; and
   at least one marker disposed on the frame proximate the edge in a location corresponding with each partially-overlapping portion of adjacent acquired individual radiation images, whereby the at least one marker is exposed onto the detector to provide an exposed mark on the acquired radiation image that can be digitally detected to identify a particular location within the overlapping portions of the adjacent acquired individual radiation images.

2. The apparatus of claim 1 wherein the detector is mounted for movement by the transport mechanism in a vertical direction.

3. The apparatus of claim 1 including a plurality of markers each aligned with corresponding partially-overlapping positions of the detector in two adjacent positions, thereby providing a plurality of imaged marks in the overlapping portions of adjacent acquired individual radiation images, whereby digitally superimposing the plurality of markers causes the adjacent acquired individual images to be properly positioned relative to one another to provide the composite image.

4. The apparatus of claim 3 wherein the detector is movable vertically between three exposure positions: a lower position, a central position, and an upper position, the apparatus including a pair of markers positioned in the overlapping portion between the lower position and the central position, the apparatus including a pair of markers positioned in the overlapping portion between the central position and the upper position, whereby the image acquired by the detector at the lower position includes a single pair of imaged marks only in its upper partially-overlapping portion, whereby the image acquired by the detector at the central position includes a pair of imaged marks in its upper partially-overlapping portion and a pair of imaged marks in its lower partially-overlapping portion, and whereby the image acquired by the detector at the upper position includes a single pair of imaged marks only in its lower partially-overlapping portion.

5. The apparatus of claim 4 wherein the all the imaged marks serve as digitally detectable reference points to facilitate digital manipulation of the individual radiation images to generate the composite image.

* * * * *